United States Patent
Klinkhammer et al.

(10) Patent No.: US 9,068,152 B2
(45) Date of Patent: Jun. 30, 2015

(54) CLEANING COMPOSITION HAVING HIGH SELF-ADHESION AND PROVIDING RESIDUAL BENEFITS

(71) Applicant: S. C. Johnson & Son, Inc., Racine, WI (US)

(72) Inventors: Michael E. Klinkhammer, Racine, WI (US); Thomas A. Strash, Kenosha, WI (US); John R. Wietfeldt, Franksville, WI (US); Russell B. Wortley, Kenosha, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 14/616,901

(22) Filed: Feb. 9, 2015

(65) Prior Publication Data

US 2015/0152355 A1    Jun. 4, 2015

Related U.S. Application Data

(63) Continuation of application No. 13/374,875, filed on Jan. 20, 2012, now Pat. No. 8,980,813, which is a continuation-in-part of application No. 12/388,576, filed on Feb. 19, 2009, now Pat. No. 8,143,205.

(60) Provisional application No. 61/064,182, filed on Feb. 21, 2008.

(51) Int. Cl.
| | |
|---|---|
| *C11D 1/72* | (2006.01) |
| *C11D 1/83* | (2006.01) |
| *C11D 7/24* | (2006.01) |
| *C11D 1/66* | (2006.01) |
| *C11D 3/18* | (2006.01) |
| *A01N 25/24* | (2006.01) |

(52) U.S. Cl.
CPC .. *C11D 1/66* (2013.01); *C11D 3/18* (2013.01); *A01N 25/24* (2013.01)

(58) Field of Classification Search
CPC .............. C11D 1/72; C11D 1/83; C11D 7/24; C11D 11/0023; C11D 11/0094; C11D 17/0056; C11D 17/0043
See application file for complete search history.

(56) References Cited

U.S. PATENT DOCUMENTS

| | | | | |
|---|---|---|---|---|
| 3,955,986 | A * | 5/1976 | Miller .............................. | 106/11 |
| 6,407,051 | B1 * | 6/2002 | Smith et al. .................... | 510/417 |
| 6,440,924 | B1 * | 8/2002 | Jeschke et al. ................ | 510/417 |
| 2002/0037824 | A1 * | 3/2002 | Smets et al. ................... | 510/305 |
| 2011/0112006 | A1 * | 5/2011 | Cobb et al. .................... | 510/405 |

* cited by examiner

*Primary Examiner* — Charles Boyer

(57) ABSTRACT

A composition for treating a hard surface. The composition has: (a) at least one adhesion promoter; (b) at least one surfactant selected from the group consisting of: anionic, nonionic, cationic, amphoteric, zwitterionic, and combinations thereof; (c) mineral oil; (d) water; (e) optionally, at least one solvent; and wherein the composition is self-adhering upon application to a surface to be treated, and wherein the composition provides a wet film to said surface when water passes over said composition and surface.

12 Claims, 6 Drawing Sheets

CLEANING COMPOSITION HAVING HIGH SELF-ADHESION AND PROVIDING RESIDUAL BENEFITS

CROSS REFERENCE TO RELATED APPLICATIONS

This application claims benefit of and is a continuation of non-provisional application U.S. Ser. No. 13/374,875 filed Jan. 20, 2012, which is a continuation-in-part of non-provisional application U.S. Ser. No. 12/388,576 filed Feb. 19, 2009 under 35 U.S.C. §120 (now U.S. Pat. No. 8,143,205 B2), which in turn claims benefit of U.S. Provisional Application No. 61/064,182, filed Feb. 21, 2008 under 35 U.S.C. §119(e).

REFERENCE REGARDING FEDERALLY SPONSORED RESEARCH OR DEVELOPMENT

Not applicable.

SEQUENTIAL LISTING

Not applicable.

FIELD OF INVENTION

In some embodiments, the invention is directed to a self-adhering composition that may provide residual benefits based on an extended spreading or coating provided by the composition upon exposure to a layer of water. In addition, the composition has improved stability under varying conditions of temperature and humidity, as well as improved self-adhesion to hard surfaces, for example a ceramic surface, such as toilet bowls, glass, windows, doors, shower or bath walls, and the like.

BACKGROUND OF INVENTION

It is known to hang cleaning and/or disinfecting and/or fragrancing agents in a container under the rim of a toilet bowl by appropriate hanging devices from which the sanitary agents are released upon each flush into the toilet bowl.

While effective, some consumers do not use such devices because of reasons such as the need to remove a used device by hand. For example, consumers may perceive such requirement as unsanitary or generally unappealing. Additionally, only one device may be used at a time in a toilet bowl and such devices tend to release composition locally, resulting in an effect that may be limited by the location and flow of the water.

In addition, consumers may shy away from using conventional under-the-rim toilet bowl hanging devices because such devices may impede the consumer during the course of a regular cleaning. During cleaning with a toilet bowl brush, a hanging device may be easily displaced and then must be put back in place by using the consumers' hands, which may be perceived as unhygienic or unappealing.

Exemplary sanitary agents for dispensing in toilet bowls may be in the form of solid blocks, liquids, and gel form.

U.S. Pat. No. 6,667,286 discloses a sanitary agent in paste or gel form which provides a long-lasting cleaning and/or deodorant-releasing and/or disinfecting effect and which can be applied directly to the surface of a toilet bowl in a simple and hygienic manner. U.S. Pat. App. Pub. No. 2008/0190457 discloses a self-sticking cleansing block that may be applied directly to the surface of a toilet bowl. The present invention provides an improvement to such a sanitary agent by providing greater stability, e.g. longevity in use, as well as improved self-adhesion to hard surfaces, especially ceramic surfaces such as a toilet bowl.

In some embodiments, the present invention provides consumers with the benefit of delivering a composition or active ingredient to a relatively wide area of a toilet bowl or other hard surface. In other nonlimiting embodiments, the present invention provides consumers with the benefit of efficiently delivering a composition or active ingredient to a relative wide area of the toilet bowl or other hard surface.

SUMMARY OF THE INVENTION

In a first nonlimiting embodiment, the present invention relates to a composition for treating a hard surface. The composition has: (a) at least one adhesion promoter; (b) at least one surfactant selected from the group consisting of: anionic, non-ionic, cationic, amphoteric, zwitterionic, and combinations thereof; (c) mineral oil; (d) water; (e) optionally, at least one solvent; and wherein the composition is self-adhering upon application to a surface to be treated, and wherein the composition provides a wet film to said surface when water passes over said composition and surface.

In a second nonlimiting embodiment, the present invention relates to a composition for treating a hard surface. The composition has: (a) about 18 wt. % to about 27 wt. % of at least one adhesion promoter; (b) about 7.5 wt. % to about 20 wt. % of at least one surfactant selected from the group consisting of: anionic, non-ionic, cationic, amphoteric, zwitterionic, and combinations thereof; (c) from 0 to about 5 wt. % of mineral oil; (d) a balance of water; (e) optionally, 0 to about 5 wt. % of at least one solvent; wherein the composition is self-adhering upon application to a surface to be treated, and wherein the composition provides a wet film to said surface when water passes over said composition and surface.

In a third nonlimiting embodiment, the present invention relates to a composition for treating a hard surface. The composition has: (a) an ethoxylated alcohol; (b) an alkyl polyglycol ether; (c) mineral oil; (d) an alcohol; (e) polyethylene glycol; (f) an alkyl ether sulfate salt; and (g) water; wherein said composition is self-adhering to a surface upon application thereto and provides a wet film on said surface when water passes over said composition and surface.

In a fourth nonlimiting embodiment, the present invention relates to a composition for application to at least one predetermined position on a hard surface and is composed to be self-adhering to said hard surface through a plurality of periodic flows of water over said composition and said hard surface, said composition partially dissolving during and after each of said periodic flows of water and providing thereby a wet film which emanates in all directions from said composition over said hard surface and, said composition including at least one surfactant which delivers in the wet film at least one active agent present in said composition to extended areas on said hard surface away from said predetermined position for immediate and residual action by said at least one active agent.

In a fifth nonlimiting embodiment, the present invention relates to a self-adhering cleaning composition for treating a hard surface comprising at least one adhesion promoter, at least one anionic surfactant, at least one nonionic surfactant which optionally in part or all also provides said at least one adhesion promoter, mineral oil, and water; wherein said hard surface is hydrophobic or is rendered hydrophobic, and wherein upon application of said composition to said hard surface and water flow over said composition, said composition partially dissolves and provides a wet film which emanates in all directions along the hard surface from said composition to extended areas on said hard surface away from said composition and is temporarily retained on said extended areas to provide residual cleaning treatment of said hard surface.

In a sixth nonlimiting embodiment, the present invention relates to a composition for treating a hard surface. The composition has: (a) one or more components which render the composition self-adhering to a hard surface to being treated by said composition, including at least one nonionic surfactant; (b) at least one surfactant selected from the group consisting of: anionic, nonionic, cationic, amphoteric, zwitterionic, and combinations thereof; (c) mineral oil; (d) water; and (e) optionally at least one active agent, wherein said at least one anionic surfactant and said at least one nonionic surfactant are present in a combined amount to provide, following a flow of water over said composition when adhered to a hard surface, a wet film which emanates from said composition over said hard surface, said wet film providing a delivery vehicle for components of said composition for immediate and residual treatment of said hard surface.

BRIEF DESCRIPTION OF THE DRAWINGS

The following detailed description of specific nonlimiting embodiments of the present invention can be best understood when read in conjunction with the following drawings, where like structures are indicated with like reference numerals and in which.

DETAILED DESCRIPTION OF THE INVENTION

Definitions

Figure 1:
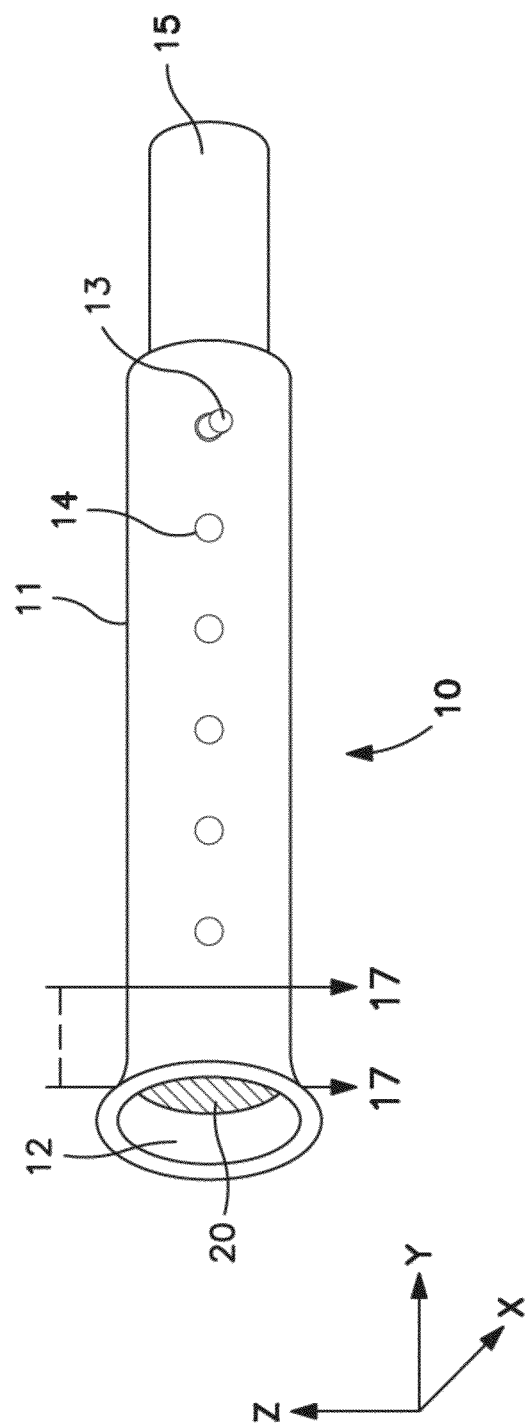
FIG. 1 shows perspective view of an exemplary gel dispensing apparatus according to the present invention.
Figure 2A:
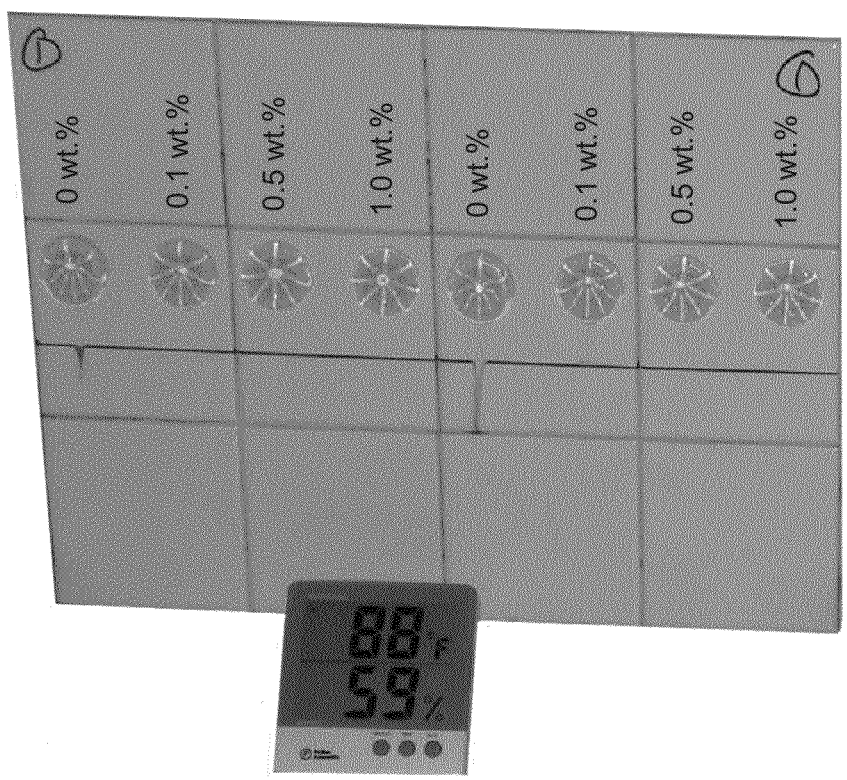
FIGS. 2A-E shows gel compositions having different mineral oil compositions at different times under test conditions as described below.
Figure 2B:
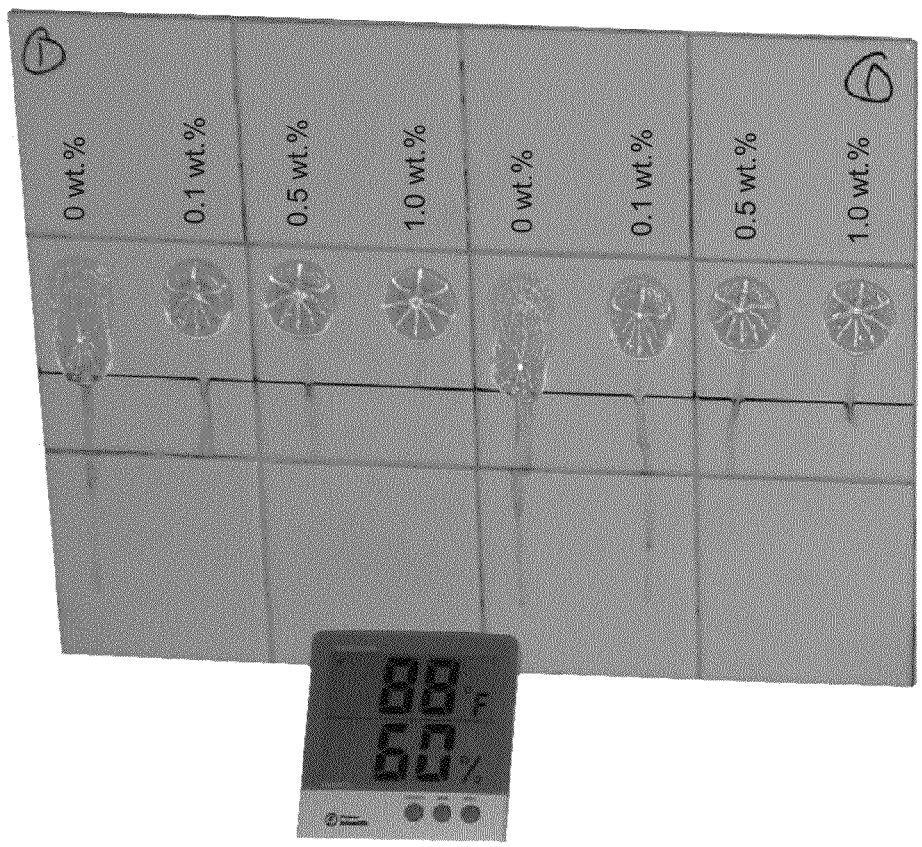
Figure 2C:
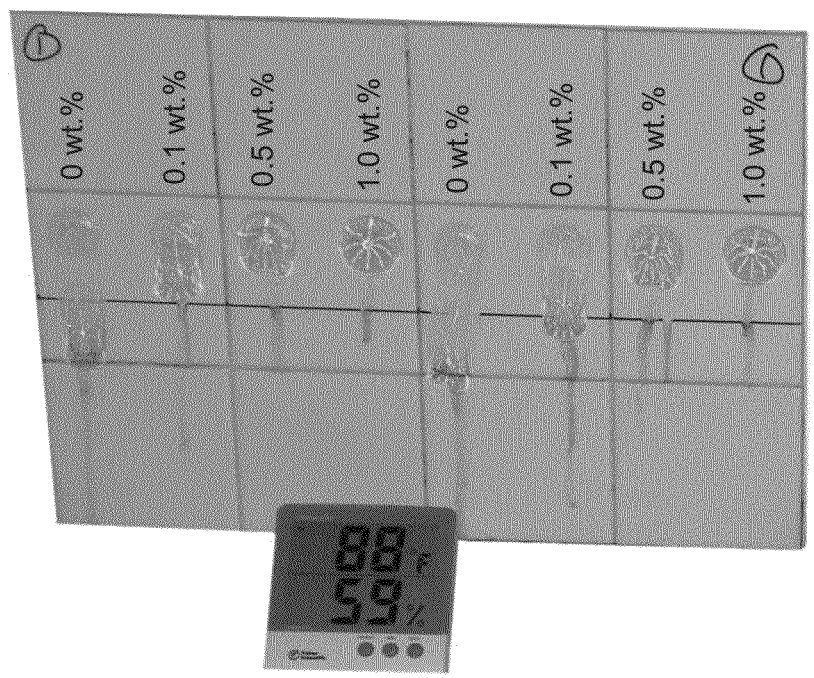
Figure 2D:
Figure 2E:
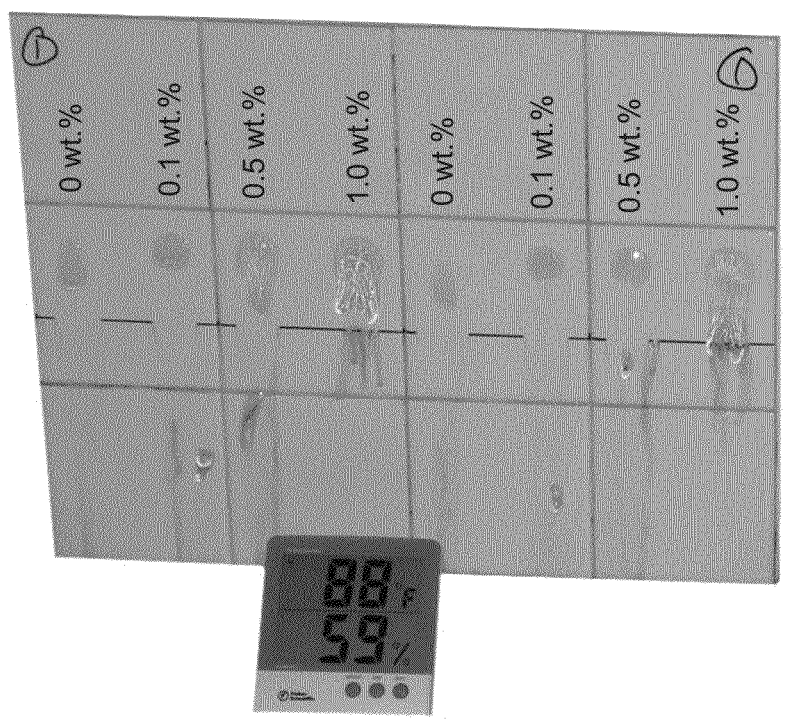

As used herein, "composition" refers to any solid, gel and/or paste substance having more than one component.

As used herein, "self adhesive" refers to the ability of a composition to stick onto a hard surface without the need for a separate adhesive or other support device. In one embodiment, a self adhesive composition does not leave any residue or other substance (i.e., additional adhesive) once the composition is used up.

As used herein, "gel" refers to a disordered solid composed of a liquid with a network of interacting particles or polymers which has a non-zero yield stress.

As used herein, "fragrance" refers to any perfume, odor-eliminator, odor masking agent, the like, and combinations thereof. In some embodiments, a fragrance is any substance which may have an effect on a consumer, or user's, olfactory senses.

As used herein, "wt. %" refers to the weight percentage of actual active ingredient in the total formula. For example, an off-the-shelf composition of Formula X may only contain 70% active ingredient X. Thus, 10 g. of the off-the-shelf composition only contains 7 g. of X. If 10 g. of the off-the-shelf composition is added to 90 g. of other ingredients, the wt. % of X in the final formula is thus only 7%.

As used herein, "hard surface" refers to any porous and/or non-porous surface. In one embodiment, a hard surface may be selected from the group consisting of: ceramic, glass, metal, polymer, stone, and combinations thereof. In another embodiment, a hard surface does not include silicon wafers and/or other semiconductor materials. Nonlimiting examples of ceramic surfaces include: toilet bowl, sink, shower, tile, the like, and combinations thereof. A nonlimiting example of a glass surfaces includes: window and the like. Nonlimiting examples of metal surfaces include: drain pipe, sink, automobiles, the like, and combinations thereof. Nonlimiting examples of a polymeric surface includes: PVC piping, fiberglass, acrylic, Corian®, the like, and combinations thereof. A nonlimiting example of a stone hard surface includes: granite, marble, and the like.

A hard surface may be any shape, size, or have any orientation that is suitable for its desired purpose. In one nonlimiting example, a hard surface may be a window which may be oriented in a vertical configuration. In another nonlimiting example, a hard surface may be the surface of a curved surface, such as a ceramic toilet bowl. In yet another nonlimiting example, a hard surface may be the inside of a pipe, which has vertical and horizontal elements, and also may have curved elements. It is thought that the shape, size and/or orientation of the hard surface will not affect the compositions of the present invention because of the unexpectedly strong transport properties of the compositions under the conditions described infra.

As used herein, "surfactant" refers to any agent that lowers the surface tension of a liquid, for example water. Exemplary surfactants which may be suitable for use with the present invention are described infra. In one embodiment, surfactants may be selected from the group consisting of anionic, nonionic, cationic, amphoteric, zwitterionic, and combinations thereof. In one embodiment, the present invention does not comprise cationic surfactants. In other nonlimiting embodiments, the surfactant may be a superwetter. One of skill in the art will appreciate that in some embodiments, a substance which may be used as an adhesion promoter may also be a surfactant.

In use, the composition of the invention may be applied directly on the hard surface to be treated, e.g. cleaned, such as a toilet bowl, shower or bath enclosure, drain, window, or the like, and self-adheres thereto, including through a plurality of flows of water passing over the self-adhering composition and surface, e.g. flushes, showers, rinses or the like. Each time water flows over the composition, a portion of the composition is released into the water that flows over the composition. The portion of the composition released onto the water covered surface provides a continuous wet film to the surface to in turn provide for immediate and long term cleaning and/or disinfecting and/or fragrancing or other surface treatment depending on the active agent(s) present in the composition. It is thought that the composition, and thus the active agents of the composition, may spread out from or are delivered from the initial composition placement in direct contact with the surface to coat continuously an extended area on the surface. The wet film acts as a coating and emanates from the self-adhering composition in all directions, i.e., 360°, from the composition, which includes in a direction against the flow of the rinse water. Motions of the surface of a liquid are coupled with those of the subsurface fluid or fluids, so that movements of the liquid normally produce stresses in the surface and vice versa. The mechanism for the movement of the gel and/or the active ingredients is discussed in greater detail infra.

Surprisingly, it is observed that the nonlimiting exemplary compositions of the present invention provide for a more rapid and extended self-spreading. Without wishing to be limited by theory, it is thought that the self-spreading effect may be modified through the addition of specific surfactants to the composition. Nonlimiting examples of factors which are thought to affect the speed and distance of the self spreading include: the amount of surfactant present, the type of surfactant present, the combination of surfactants present, the amount of spreading of the surfactant over the water flow, the ability of the surfactant to adsorb at the liquid/air interface, and the surface energy of the treated surface. It is thought that the surfactant of the composition serves to push other molecules, e.g. compounds, around so as to deliver these compounds to other parts of the surface. Compounds desirable for extended delivery over a treated surface are active agents, e.g. agents capable of activity as opposed to being inert or static. Nonlimiting examples of active agents, or active ingredients, that may be used include: cleaning compounds, germicides, antimicrobials, bleaches, fragrances, surface modifiers, stain preventers (such as a chelator) the like, and combinations thereof. The composition is especially useful in treating the surface of a toilet bowl since it allows for delivery and retention of a desired active agent on a surface above the water line in the bowl as well as below the water line.

In some embodiments, the composition can be applied directly to a surface using any suitable applicator device, such as a pump or syringe-type device, manual, pressurized, or mechanized, aerosol, or sprayer. The consumer may activate the applicator for application of the composition directly to a surface without the need to touch the surface. In the case of a toilet bowl surface, this provides for a hygienic and easily accessible method of application. The amount and location(s) of the composition may be chosen by the user, e.g. one or more dollops or drops of composition, or one or more lines of composition. The composition self-adheres to a hard surface to which it is applied, such as the ceramic side wall of a toilet bowl or shower wall. A surprising and unique feature not provided by conventional devices is that the composition is delivered to surfaces located above the site of application of the composition to the surface.

Composition

In one embodiment, the composition has a gel or gel-like consistency. In the described embodiment, the composition is, thus, firm but not rigid as a solid. In an alternative embodiment, the composition is a solid. In still another embodiment, the composition is a malleable solid.

The improved adhesion obtained by the composition of the invention allows application on a vertical surface without becoming detached through a plurality of streams of rinse water and the gradual washing away of a portion of the composition over time to provide the desired cleaning and/or disinfecting and/or fragrance or other treatment action. Once the composition is completely washed away, nothing remains for removal and more composition is simply applied.

In some embodiments, the composition may include an adhesion promoter which causes a bond with water and gives the composition a dimensional stability even under the action of rinse water; at least one nonionic surfactant (which may serve all or in part as the adhesion promoter), preferably an ethoxylated alcohol; at least one anionic surfactant, preferably an alkali metal alkyl ether sulfate or sulfonate; mineral oil; water; and optionally at least one solvent. More particularly, the hydrophilic polymer holds the composition to the surface to enhance the maintenance and thereby extend the times of spreading and, thus, delivery of active agents for treatment of the surface and/or surrounding environment. In some embodiments, the composition may also include a superwetter compound to enhance the spreading of the wet film. The composition displays extended durability without the necessity of an exterior hanging device or holder thereby only requiring a new application of the composition to the surface after a long lapse of time and no need to remove any device.

In some nonlimiting examples, there are a number of components of the present invention composition that are suitable for treating hard surfaces. In one embodiment, the composition comprises an adhesion promoter present in an amount of from about 20 wt. % to about 80 wt. %. In another embodiment, the composition comprises an adhesion promoter in the amount of from about 20 wt. % to about 60 wt. %. In another embodiment, the composition comprises an adhesion promoter in the amount of from about 40 wt. % to about 60 wt. %. In an alternative embodiment, the composition comprises an adhesion promoter in the amount of from about 20 wt. % to about 30 wt. %.

In another embodiment, the composition comprises at least one surfactant in an amount of greater than 7.5 wt. %. In another embodiment, the composition comprises at least one surfactant in an amount of from about 7.5 wt. % to about 20 wt. %. Surprisingly, it is discovered that providing an optimal amount of surfactant, in particular anionic surfactant, provides the product with a particularly strong "foaming" characteristic that greatly pleases consumers.

In one embodiment, the composition comprises a non-polar hydrocarbon such as mineral oil in an amount of less than about 5 wt. %. In another embodiment, the composition comprises mineral oil in an amount of from greater than zero wt. % to about 5 wt. %. In another embodiment, the composition comprises mineral oil in an amount of from about 0.5 wt. % to about 3 wt. %. In some embodiments, the compositions may be brought to 100 wt. % using any suitable material for the intended application. One of skill in the art will appreciate that this may include, but not be limited to, a balance of water, surface modifiers, germicides, bleaches, cleaners, foamers, the like, and combinations thereof.

Optionally, the compositions of the present invention may further comprise at least one solvent in an amount of from 0 wt. % to about 15 wt. % and the composition may further comprise at least one fragrance in an amount of from 0 wt. % to about 15 wt. %. Additionally, the composition may optionally include a hydrophilic polymer in an amount from 0 wt. % to about 5 wt. % to amplify transport effects of the composition. In one embodiment, "solvent" does not include water.

A further optional component is a superwetter. Without wishing to be limited by theory, it is thought that a superwetter may enhance the wet film provided in use of the composition. Superwetters, as may be used in the present invention composition, are described in greater detail infra. In other nonlimiting embodiments, additional optional components include conventional adjuvants, such as a preservative, colorant, foam stabilizer, antimicrobial, germicide, or the like, present in an effective amount.

Exemplary components suitable for use as an adhesion promoter may have long or long-chained molecules, for the most part linear, that are at least in part hydrophilic and thus include at least a hydrophilic residual or a hydrophilic group so as to provide interaction with water molecules. Preferably, the adhesion promoter has unbranched molecules to form a desired network-like structure to form adhesion-promoting molecules. The adhesion promoter may be totally hydrophilic or partly hydrophilic, partly hydrophobic.

Exemplary pure adhesion hydrophilic promoters suitable for use in the present invention include, for example: polyethylene glycol, cellulose, especially sodium carboxymethyl cellulose, hydroxyethyl cellulose, hydroxypropyl cellulose, or polysaccharides such as xanthan gum, agar, gellan gum, acacia gum, carob bean flour, guar gum or starch. Polysaccharides can form networks with the necessary solidity and a sufficient stickiness in concentrations of from 0 wt. % to about 10 wt. %; from 0 wt. % to about 5 wt. %; and from about 1 wt. % to about 2 wt. %.

The adhesion-promoting molecules can be synthetic or natural polymers, for instance, polyacrylates, polysaccharides, polyvinyl alcohols, or polyvinyl pyrrolidones. It is also possible to use alginates, diurethanes, gelatines, pectines, oleyl amines, alkyl dimethyl amine oxides, or alkyl ether sulfates.

Organic molecules with a hydrophilic and hydrophobic end may also be used as adhesion promoters. As hydrophilic residuals, for example, polyalkoxy groups, preferably polyethoxy, polypropoxy, or polybutyoxy or mixed polyalkoxy groups such as, for example, poly(ethoxypropoxy) groups can be used. Especially preferred for use as a hydrophilic end, for example, is a polyethoxy residual including from 15 to 55 ethoxy groups, preferably from 25 to 45 and more preferably from 30 to 40 ethoxy groups.

In some embodiments, anionic groups, for example, sulfonates, carbonates, or sulfates, can be used as hydrophilic ends. In other embodiments, stearates, especially sodium or potassium stearate, are suitable as adhesion promoters.

In embodiments wherein the adhesion-promoting molecules also have a hydrophobic end, straight-chained alkyl residuals are preferred for the hydrophobic residual, whereby in particular even-numbered alkyl residuals are preferred because of the better biological degradability. Without wishing to be limited by theory, it is thought that to obtain the desired network formation of the adhesion-promoting molecules, the molecules should be unbranched.

If alkyl residuals are chosen as hydrophobic residuals, alkyl residuals with at least 12 carbon atoms are preferred. More preferred are alkyl chain lengths of from 16 to 30 carbon atoms, most preferred is from 20 to 22 carbon atoms.

Exemplary adhesion promoters are polyalkoxyalkanes, preferably a mixture of C20 to C22 alkyl ethoxylate with from 18 to 50 ethylene oxide groups (EO), preferably from about 25 to about 35 EO, and also sodium dodecylbenzene sulfonate. With a reduction of the number of alkoxy groups the adhesion promoter becomes more lipophilic, whereby, for example, the solubility of perfume and thus the intensity of the fragrance can be raised.

Molecules that generally act like thickeners in aqueous systems, for example, hydrophilic substances, can also be used as adhesion promoters.

Without wishing to be limited by theory, it is thought that the concentration of the adhesion promoter to be used depends on its hydrophilicity and its power to form a network. When using polysaccharides, for example, concentrations from about 1 wt. % to about 2 wt. % of the adhesion promoter can be sufficient, whereas in embodiments comprising polyalkoxyalkanes the concentrations may be from about 10 wt %. to about 40 wt. %; in another embodiment from about 15 wt. % to about 35 wt. %; and in another embodiment still from about 20 wt. % to about 30 wt. %.

Also without wishing to be limited by theory, it is thought that in order to produce the desired number of adhering sites with the adhesion-promoting molecules through the absorption of water, the composition may contain at least about 25% by weight water, and optionally additional solvent. In one embodiment, the composition comprises water from about 40 wt. % to about 65 wt. %. One of skill in the art will appreciate that the amount of water that is to be used is dependent on, among other things, the adhesion promoter used and the amount of adjuvants also in the formula.

Exemplary anionic surfactants suitable for use include alkali metal $C_6$-$C_{18}$ alkyl ether sulfates, e.g. sodium lauryl ether sulfate; α-olefin sulfonates or methyl taurides. Other suitable anionic surfactants include alkali metal salts of alkyl, alkenyl and alkylaryl sulfates and sulfonates. Some such anionic surfactants have the general formula $RSO_4M$ or $RSO_3M$, where R may be an alkyl or alkenyl group of about 8 to about 20 carbon atoms, or an alkylaryl group, the alkyl portion of which may be a straight- or branched-chain alkyl group of about 9 to about 15 carbon atoms, the aryl portion of which may be phenyl or a derivative thereof, and M may be an alkali metal (e.g., ammonium, sodium, potassium or lithium).

Exemplary nonionic sulfactants suitable for use include $C_{20}$-$C_{22}$ alkyl ethoxylate with 18 to 50 ethylene oxide groups (EO). In another embodiment, $C_{20}$-$C_{22}$ alkyl ethoxylate comprise 25 to 35 ethylene oxide groups, preferably as an adhesion promoter and nonionic surfactant.

Additional nonlimiting examples of other nonionic surfactants suitable for use include alkylpolyglycosides such as those available under the tradename GLUCOPON from Henkel, Cincinnati, Ohio, USA. The alkylpolyglycosides have the following formula: $RO-(R'O)_x-Z_n$ where R is a monovalent alkyl radical containing 8 to 20 carbon atoms (the alkyl group may be straight or branched, saturated or unsaturated), O is an oxygen atom, R' is a divalent alkyl radical containing 2 to 4 carbon atoms, preferably ethylene or propylene, x is a number having an average value of 0 to 12, Z is a reducing saccharide moiety containing 5 or 6 carbon atoms, preferably a glucose, galactose, glucosyl, or galactosyl residue, and n is a number having an average value of about 1 to 10. For a detailed discussion of various alkyl glycosides see U.S. Statutory Invention Registration H468 and U.S. Pat. No. 4,565,647, which are incorporated herein by reference. Some exemplary GLUCOPONS are as follows (where Z is a glucose moiety and x=0) in Table A.

TABLE A

| Exemplary Glucopons | | |
|---|---|---|
| Product | N | R (# carbon atoms) |
| 425N | 2.5 | 8-14 |
| 425LF | 2.5 | 8-14 (10 w/w % star-shaped alcohol added) |
| 220UP | 2.5 | 8-10 |
| 225DK | 2.7 | 8-10 |
| 600UP | 2.4 | 12-14 |
| 215CSUP | 2.5 | 8-10 |

Other nonlimiting examples of nonionic surfactants suitable for use include alcohol ethoxylates such as those available under the trade name LUTENSOL from BASF, Ludwigshafen, Germany. These surfactants have the general formula $C_{13}H_{25}/C_{15}H_{27}-OC_2H_4)_n-OH$ (the alkyl group being a mixture of $C_{13}/C_{15}$). Especially preferred are LUTENSOL AO3 (n=3), AO8 (n=8), and AO10 (n=10). Other alcohol ethoxylates include secondary alkanols condensed with $(OC_2H_4)$ such as TERGITOL 15-S-12, a $C_{11}$-$C_{15}$ secondary alkanol condensed with 12 $(OC_2H_4)$ available from Dow Surfactants. Another example of a nonionic surfactant suitable for use is polyoxyethylene (4) lauryl ether. Amine oxides are also suitable.

At least one solvent can be present in the composition to assist in blending of surfactants and other liquids. The solvent is present in an amount of from about 0 wt. % to about 15 wt. %, preferably from about 1 wt. % to about 12 wt. %, and more preferably in an amount from about 5 wt. % to about 10 wt. %.

Examples of solvents suitable for use are aliphatic alcohols of up to 8 carbon atoms; alkylene glycols of up to 6 carbon atoms; polyalkylene glycols having up to 6 carbon atoms per alkylene group; mono- or dialkyl ethers of alkylene glycols or polyalkylene glycols having up to 6 carbon atoms per glycol group and up to 6 carbon atoms in each alkyl group; and mono- or diesters of alkylene glycols or polyalkylene glycols having up to 6 carbon atoms per glycol group and up to 6 carbon atoms in each ester group. Specific examples of solvents include t-butanol, t-pentyl alcohol; 2,3-dimethyl-2-butanol, benzyl alcohol or 2-phenyl ethanol, ethylene glycol, propylene glycol, dipropylene glycol, propylene glycol mono-n-butyl ether, dipropylene glycol mono-n-butyl ether, propylene glycol mono-n-propyl ether, dipropylene glycol mono-n-propyl ether, diethylene glycol mono-n-butyl ether, diethylene glycol monomethyl ether, dipropylene glycol monomethyl ether, triethylene glycol, propylene glycol monoacetate, glycerin, ethanol, isopropanol, and dipropylene glycol monoacetate. One preferred solvent is polyethylene glycol.

It is thought that the inclusion of a non-polar hydrocarbon, such as mineral oil, may serve to achieve increased stability and self-adherence to a hard surface, especially a ceramic surface. The mineral oil is present in an amount of greater than 0% by weight to about 5% by weight, based on the total weight of the composition. In one embodiment, mineral oil is present in an amount of from about 0.5% wt. % to about 3.5 wt. %. In another embodiment, mineral oil is present in an amount of from about 0.5 wt. % to about 2 wt. %. The amount of mineral oil to be included will depend on the adhesion performance of the balance of the formula. Without wishing to be limited by theory, it is thought that as the amount of mineral oil is increased, the adhesion is also increased.

Although it provides benefits when used in the composition, it is also thought that the inclusion of the mineral oil in higher amounts without decreasing the amount of surfactant and/or thickener and/or adhesion promoters will result in the composition being thickened to a degree which makes processing of the composition during manufacture and use difficult because the firmness of the composition makes it difficult to process. In manufacture, the processing can be carried out under increased temperatures, but such also increases the cost of manufacture and creates other difficulties due to the increased temperature level.

Nonlimiting examples of hydrophilic polymers useful herein include those based on acrylic acid and acrylates, such as, for example, described in U.S. Pat. Nos. 6,593,288, 6,767, 410, 6,703,358 and 6,569,261. Suitable polymers are sold under the trade name of MIRAPOL SURF S by Rhodia. A preferred polymer is MIRAPOL SURF 5-500.

A superwetter is optionally included in the composition to enhance the maintenance of the wet film provided. A superwetter may thereby assist in decreasing the time of spreading. Examples of superwetters suitable for inclusion in the composition hydroxylated dimethylsiloxanes such as Dow Corning Q2-5211 (Dow Corning, Midland, Mich.). The superwetter(s) may be present (in addition to any other surfactant in the composition) in an amount of 0 to about 5 wt. %; preferably from about 0.01 to about 2 wt. %, and most preferably from about 0.1 wt. % to about 1 wt. %.

Fragrances and aromatic substances can be included in the composition to enhance the surrounding atmosphere.

In one embodiment, a gel composition comprises less than 6 wt. % fragrance. In another embodiment, the gel composition comprises from 0 wt. % to 6 wt. % fragrance. In another embodiment still, the gel composition comprises from 0 wt. % to about 5 wt. % fragrance. In yet another embodiment, the gel composition comprises from about 2 wt. % to about 5 wt. % fragrance.

In one embodiment, a solid composition comprises less than 10 wt. % fragrance. In another embodiment, the solid composition comprises from 0 wt. % to 10 wt. % fragrance. In another embodiment still, the solid composition comprises from 2 wt. % to about 8 wt. % fragrance. In yet another embodiment, the gel composition comprises from about 4 wt. % to about 7 wt. % fragrance.

The composition according to the invention sticks to hard surfaces through self-adhesion. The solid, gel and gel-like materials are dimensionally stable so that they do not "run" or "drip" through a plurality of streams of water flowing thereover. It is thought that consumers prefer such a composition because the adhesion and shape of the composition remain intact even through a plurality of water rinses. Exemplary compositions comprising mineral oil are described in Table B, below:

TABLE B

Exemplary Compositions Comprising Mineral Oil

| INGREDIENTS | SAMPLE 1 | SAMPLE 2 | SAMPLE 3 | SAMPLE 4 |
|---|---|---|---|---|
| $C_{22}$ Ethoxylated Alcohol (30 EO) | 13 | 13 | 13 | 13 |
| $C_{16-18}$ Ethoxylated Alcohol (30 EO) | 13 | 13 | 13 | 13 |
| Preservative | 0.15 | 0.15 | 0.15 | 0.15 |
| Dionized Water | 44.85 | 44.75 | 44.35 | 43.85 |
| Mineral Oil | 0 | 0.1 | 0.5 | 1.0 |
| Glycerine | 5 | 5 | 5 | 5 |
| Polyethylene Glycol 6000 | 1 | 1 | 1 | 1 |
| Sodium lauryl ether sulfate | 18 | 18 | 18 | 18 |
| Fragrance | 5 | 5 | 5 | 5 |
| Total Wt. % | 100 Wt. % | 100 Wt. % | 100 Wt. % | 100 Wt. % |

Transport of Active Ingredients

As described supra, the composition of the invention may be applied directly on the surface of a sanitary object to be cleaned, such as a toilet bowl, shower or bath enclosure, or the like, and self-adheres thereto through a plurality of streams of water flowing over the self-adhering composition, e.g. flushes or showers. Each time water flows over the composition, a portion of the composition is released onto the surface to which the composition adheres as well as into the water to provide long term cleaning, disinfecting, fragrancing, stain prevention, surface modification, UV protection, whitening, bleaching, and the like. It is thought that any residual benefits may be obtained from the composition through the inclusion of ingredients described above which provide for the spreading and/or transport of the composition along the hard surface to areas wherein the composition was not originally deposited. More specifically, the composition, and thus the active agents of the composition, spread out from or are delivered from the initial composition placement in direct contact with the surface to coat an extended adjoining area on the surface. Motions of the surface of a liquid are coupled with those of the subsurface fluid or fluids, so that movements of the liquid normally produce stresses in the surface and vice versa. The movement of the surface and of the entrained fluid(s) caused by surface tension gradients is called the Marangoni effect (IUPAC Compendium of Chemical Terminology, 2nd Edition, 1994). Thus, the composition of the invention provides that liquid flows along a liquid-air interface from areas having low surface tension to areas having higher surface tension. The Marangoni flow is macroconvection, i.e., the gradient in the interfacial tension is imposed on the system by an asymmetry, as opposed to microconvection where the flow is caused by a disturbance that is amplified in time (an instability). Thus, upon a flow of water over the composition of the invention, the composition spreads outward to cover extended adjoining surface areas as opposed to only the local area covered by or immediately adjacent the composition.

More specifically, it is thought that this effect is observed due to mass transfer on, or in, a liquid layer due to differences in surface tension on that liquid layer. Without wishing to be limited by theory, it is thought that because a liquid with a relatively high surface tension pulls more strongly on the surrounding liquid compared to a liquid with a relatively low surface tension, a surface tension gradient will cause liquid to flow away from regions of relatively low surface tension towards regions of relatively high surface tension. Such property, the Marangoni effect, is used in high-tech semiconductor wafer processing. Nonlimiting examples include U.S. Pat. Nos. 7,343,922; 7,383,843; and 7,417,016.

Those of skill in the art will appreciate that a dimensionless unit often referred to as the Marangoni number may be used to estimate the Marangoni effect, and other transport properties, of a material. One of the factors which may be used to estimate the Marangoni effect of a material, the Marangoni number, may be described by Eq. 1. One of skill in the art will appreciate that the Marangoni number provides a dimensionless parameter which represents a measure of the forces due to surface tension gradients relative to viscous forces.

$$\text{Marangoni number}, M_a = -\Gamma (d\sigma/dc)/D\mu$$

Where
$M_a$ is the Marangoni number
$\Gamma$ is the surface excess concentration of surfactant (mol/m$^2$)
$\sigma$ is the surface tension (N/m)
c is the bulk surfactant concentration (mol/m$^3$)
$\mu$ is the bulk dynamic viscosity (Pascal seconds)
D is the bulk surfactant diffusion coefficient (m$^2$/s)

As described supra, there exist a number of compositions that are used to transport active ingredients around a surface. However, most of the aforementioned compositions rely on gravity or the adhesion-cohesion of liquids as the lone mechanisms for transporting the composition around the surface. Similarly, traditional liquid bathroom cleaners or similar compositions in the bath cleaning arts, for example, often require the user to use a brush, other implement, to manually spread the composition around the surface.

Surprisingly, it was discovered that, despite the complexity associated with transport phenomena, the transport properties of a composition could be enhanced through the addition of specific surfactants and other ingredients, to the composition. Even more surprisingly, the composition may be used as a vehicle for active ingredients when the composition is in the presence of a liquid layer.

With respect to a hard surface, such as a toilet bowl, it is thought that by providing a composition according to the present invention, one may be able to provide consumers with additional benefits of limiting the amount of touching or other interaction between the consumer and the toilet bowl. Such minimal interaction may be achieved by taking advantage of the composition's ability to move from one area of the toilet (or other hard surface) via gradients in surface tension which may be induced by the surfactants. Thus, it is thought that when a user flushes a toilet, the interaction of the liquid layer (from the flush) with the composition will cause the gel composition to migrate along the surface tension gradient, thus moving the composition around the toilet.

One of skill in the art will appreciate that the transport mechanism described above may be used with any hard surface that is provided with a liquid layer and is not necessarily limited to use in a toilet bowl. For example, it is hypothesized that a user may be able to provide a composition to the surface of a sink, window, drain, or any other hard surface on which water, or other liquid, may be provided. Additional exemplary surfaces are described throughout.

Considerations for Treatment of Hard Surfaces

The self-spreading of the composition to provide a coating effect and residual benefits from active treating agents, is based on the surfactant(s) present in the composition. Nonlimiting factors which may be thought to affect the speed and distance of the self-spreading, in addition to the essential requirements of direct contact of the composition with the surface to be treated and a flow of water over and around the composition, are the amount and type of surfactant present, in addition to and the amount or rate of dissolution of the surfactant in the water flow.

It is surprisingly discovered that when the surfactant amount and dissolution are controlled as described above, the product is capable of covering an extended area outward 360° from the area of initial product application. Further, in embodiments including active ingredients, also described above, the composition may provide an initial and/or further residual treatment of a surface. The speed of spreading is significant since the extent of spreading as desired must be complete prior to drying of the water on the surface since the water is a necessary component in providing the continuous film.

Method of Use

As described above, the present invention compositions may be used to provide immediate and/or residual benefits to a hard surface upon application to that surface wherein the surface will be subject to water or some other liquid which will provide a layer for a surface energy gradient.

In one embodiment the present invention composition may be comprised of the following steps: (1) Application of one or more doses of the composition onto a hard surface; (2) Exposure of the hard surface, and subsequently the one or more doses of composition, to a liquid layer to provide a spread out and dissipated composition layer. The method for using the product may further comprise the optional steps: (3) Exposure of the hard surface, and subsequently the spread out and dissipated composition layer to a liquid layer to provide a further spread out and dissipated composition layer. One of skill in the art will appreciate that (3) may be repeated indefinitely until the composition is completely dissipated. In some embodiments, the liquid layer is water.

As described supra, the hard surface may be selected from the group consisting of: ceramic, glass, metal, polymer, fiberglass, acrylic, stone, the like and combinations thereof.

A liquid layer may be provided through any means that is suitable for the intended function. For example, in a toilet bowl, a dose of composition may be applied to the inside surface of the toilet bowl (a ceramic hard surface) and the toilet may be flushed to provide the liquid layer that is necessary to facilitate the transport of the composition around the toilet bowl. In another example, a dose of composition may be applied to the outside surface of a window. The outside surface of the window may be sprayed with water by the user using a hose or power washer, or rain may deposit a layer of water to the window. In yet another example, a dose of composition may be applied to the inside of a sink or drain pipe. The user may simply activate the faucet to provide a layer of water to the sink or drain pipe. In still another example, a dose of composition may be applied to the wall of a shower. The user may activate the shower to provide a liquid layer to the surface. In yet another example, it is envisioned that the liquid layer may also be provided with steam or a relatively high humidity.

One of skill in the art will appreciate that the different applications and embodiments of the present invention composition may be provided with different active ingredients or benefit agents which may vary depending on the desired application.

Method of Use: Dispensing Considerations

There exist applicators for gel-like substances. For example, PCT Int. Pat. App. WO 03/043906 and WO 2004/043825 disclose exemplary dispensing devices. However, while the aforementioned dispensers succeed in applying an adhesive gel-like substance to a surface, some users may find that the inability to provide consistent dosing frustrating. Specifically, consumers realize that overapplication of the product may be wasteful and lead to the purchase of unnecessary refills, while underapplication of the product may minimize the efficacy of the composition.

A nonlimiting exemplary dispenser that is capable of providing metered doses of a composition that may be compatible with the present invention compositions is described in U.S. Patent App. No. 2007/0007302A1.

Without wishing to be limited by theory, it is thought that consumers may prefer to provide the compositions of the present invention in unitized, discrete doses because such a device is relatively easy to use compared to devices wherein the consumer controls the dose size.

Further, one of skill in the art will appreciate that, when used in conjunction with a metered dispenser, the dispenser may provide doses of the composition in any volume and/or size and/or dose that is suitable for the intended application. Similarly, the shape of the dispenser may be any shape that is desired. For example, FIG. 1 illustrates an exemplary embodiment of a dispenser 10 that may be used to dispense gel composition 20 according to the present invention. The dispenser 10 comprises a cylindrical body 11 and a gel composition 20 contained therein. The dispenser 10 further comprises a resistive push-button 13 which fits a user may push into a guide hole 14, and then slide a guide member 15 in the negative-y direction to push gel composition 20 towards the dispenser mouth 12. Upon moving the guide member 15 a predetermined distance, the push-button 13 may then "pop" out of the next guide hole 14 to allow for a precise dose of composition 20 to be dispensed. The cross-section 17-17 of the dispenser 10 may be any shape that is desirable for the intended purpose. In one embodiment, the cross section 17-17 may be annular. Nonlimiting examples of cross-sectional shapes may be selected from: squares, circles, triangles, ovals, stars, the like, and combinations thereof.

In one embodiment, a composition according to the present invention may be provided in a dispenser wherein the dispenser provides unitized doses. In a particular embodiment, the unitized dose is from about 4 g/dose to about 10 g/dose. In another embodiment, the unitized dose is from about 5 g/dose to about 9 g/dose. In yet another embodiment, the dispenser may provide from about 6 to about 8 g/dose unitized doses. In still another embodiment, the dispenser may provide from about 3 to about 12 unitized doses. In some embodiments, the dispenser may be refilled with additional composition.

In embodiments wherein the composition is a solid, or a malleable solid, an exemplary method and apparatus for dispensing is described in U.S. Pat. App. No. 2008/0190457.

Experimental Results and Data

Samples

Samples 1-13 comprise a base ingredient set in addition to a surfactant. It should be noted that the amount of deionized water in the base ingredient set is adjusted to accommodate the additional surfactant in Samples 1-13. The Scrubbing Bubbles Sample describes an embodiment of a current product (Scrubbing Bubbles Toilet Gel "Citrus Scent", S.C. Johnson & Son, Racine, Wis.). The U.S. Pat. No. 6,667,286 samples are derived from Example 1 of U.S. Pat. No. 6,667,286. '286 (1) includes the Rhodopol component. '286 (2) is a sample that is made with ingredients at the midpoint of the described ranges. Measurements are made to the samples for different properties. Surprisingly, the samples comprising the surfactant, and other ingredients according to the present invention samples provide an ideal combination of various properties which are described in greater detail below:

| Base Ingredient Set ("Base"): | |
| --- | --- |
| Ingredient | Wt. % |
| Deionized Water | 64.000000 |
| $C_{22}$ Ethoxylated Alcohol (30 EO) | 13.000000 |
| $C_{16-18}$ Ethoxylated Alcohol (30 EO) | 13.000000 |
| Glycerine, USP, 99.5% | 5.000000 |
| Quest ® F560805 | 5.000000 |

| Samples | | |
| --- | --- | --- |
| Sample | Surfactant | Wt. % |
| 1 | Alkyl Polyglycoside 425 N | 2.00 |
| 2 | Pluronic ® F127 | 1.00 |
| 3 | Tergitol ® 15-S-12 | 1.03 |
| 4 | Sodium Lauryl Ether Sulfate 2EO, 70% | 1.43 |
| 5 | Q2-5211 | 1.67 |
| 6 | Leutensol ® XL140 | 1.00 |
| 7 | Leutensol ® XP 30 | 1.00 |
| 8 | Aerosol ® OT-NV | 1.20 |
| 9 | Macat ® AO-12 | 3.33 |
| 10 | Macat ® AO-8 | 3.51 |
| 11 | Tegopren ® 6922 | 2.00 |
| 12 | Alkyl Polyglycoside 425 N | 4.00 |
| 13 | Sodium Lauryl Ether Sulfate 2EO, 70% | 11.43 |
| '286 (1) | Example 1 of 6,667,286-Rhodopol | |
| '286 (2) | Example 1 of 6,667,286-Midpoints of ranges | |
| Scrubbing Bubbles | Citrus Scent | |

Surface Spreading

As described supra, the present invention compositions provides the unexpected benefit over existing compositions of, inter alia, increased mobility and transport. Exemplary compositions are made according to the Detailed Description and are tested for surface spreading using the "Surface Spreading Method" described below.

Surprisingly, it is noticed that the addition of the surfactants provide a significant increase in transport of the compositions. In one embodiment, the compositions of the present invention provide a transport rate factor of less than 55 seconds. In another embodiment, the compositions of the present invention provide a transport rate factor of less than about 50 seconds. In still another embodiment, the compositions of the present invention provide a transport rate factor of from about 0 seconds to about 55 seconds. In another embodiment, the compositions of the present invention provide a transport rate factor of from about 30 seconds to about 55 seconds. In yet still another embodiment, the compositions of the present invention provide a transport rate factor of from about 30 seconds to about 50 seconds. In still another embodiment, the compositions of the present invention provide a transport rate factor of from about 30 seconds to about 40 seconds.

Results for the surface spreading (Transport Rate Factor) of a product is reported in Table C below.

The surface spreading of a product is measured by the Surface Spreading Test described below.

TABLE C

Surface Spreading Measurements

| Sample | Transport Rate Factor |
|---|---|
| 1 | 33.2 |
| 2 | 47.7 |
| 3 | 53.3 |
| 4 | 50.5 |
| 5 | 30.4 |
| 6 | 50.1 |
| 7 | 46.3 |
| 8 | 36.9 |
| 9 | 37.0 |
| 10 | 42.7 |
| 11 | 56.9 |
| 12 | 38.5 |
| 13 | 40.2 |
| Base | 50.1 |
| '286 (1) | 65.9 |
| Scrubbing Bubbles | 39.1 |

Composition Adhesion

In addition to the mobility of the composition, it is surprisingly discovered that the ability of the composition to adhere to a hard surface provides additional unexpected benefits, such as product longevity during use. A product must have an ability to adhere to a surface for a period of at least 5 hours, as measured by the adhesion test described below. In one embodiment, a product has a minimum adhesion of greater than about 8 hours. In another embodiment, a product has a minimum adhesion of from about 8 hours to about 70 hours.

Results for the minimum adhesion of a product is reported in Table D below.

The minimum adhesion of a product is measured by the Adhesion Test described below.

TABLE D

Minimum Adhesion Measurements

| Sample | Adhesion Time (Hours) |
|---|---|
| 1 | >64 |
| 2 | >64 |
| 3 | >64 |
| 4 | >64 |
| 5 | >64 |
| 6 | >64 |
| 7 | >64 |
| 8 | >64 |
| 9 | >64 |
| 10 | >64 |
| 11 | >65 |

TABLE D-continued

Minimum Adhesion Measurements

| Sample | Adhesion Time (Hours) |
|---|---|
| 12 | >88 |
| 13 | 21.0 |
| Base | >64 |
| '286 (1) | 6.0 |
| '286 (2) | 7.5 |
| Scrubbing Bubbles | 12.0 |

Composition Gel Temperature

It is thought that an additional property which is important to compositions is the ability to maintain its form despite being subject to relatively high temperatures. Similarly to adhesion, the ability to maintain its form, and being resistant to melting. Specifically, this metric measures the temperature at which the composition transitions to a viscosity of greater than 100 cps as the composition cools. Further, having a relatively high composition gel temperature may provide processing, manufacturing, transport, and packaging advantages to producers.

In one embodiment the composition has a gel temperature of greater than 50° C. In another embodiment, the composition has a gel temperature of from about 50° C. to about 80° C. In another embodiment still, the composition has a gel temperature of from about 50° C. to about 70° C.

The composition gel temperature is measured by the Gel Temperature Test described below.

Results for the composition gel temperature of a product is reported in Table E below.

The minimum adhesion of a product is measured by the Gel Temperature Test described below.

TABLE E

Gel Temperature Measurements

| Sample | Gel Temperature (° C.) |
|---|---|
| 1 | 71.6 |
| 2 | 72.7 |
| 3 | 72.5 |
| 4 | 71.4 |
| 5 | 71.9 |
| 6 | 71.7 |
| 7 | 70.5 |
| 8 | 70.5 |
| 9 | 74.7 |
| 10 | 77.0 |
| 11 | 71.9 |
| 12 | 66.2 |
| 13 | 69.1 |
| Base | 74.1 |
| '286 (1) | 70.3 |
| '286 (2) | 70.6 |
| Scrubbing Bubbles | 57.3 |

Composition Viscosity

In some nonlimiting embodiments, the composition of the invention is in the form of a self-adhering gel or gel-like composition for treating hard surfaces. In the embodiments wherein the compositions are self-adhering gels, the viscosity of the composition is from about 150,000 centipose (cP) to about 400,000 cP.

The composition gel temperature is measured by the Viscosity Test described below.

TABLE F

Viscosity Measurements

| Sample | Viscosity (cP) |
| --- | --- |
| 1 | 187000 |
| 2 | 233000 |
| 3 | 155000 |
| 4 | 270000 |
| 5 | 188000 |
| 6 | 282000 |
| 7 | 199000 |
| 8 | 239000 |
| 9 | 208000 |
| 10 | 400000 |
| 11 | 197000 |
| 12 | 349000 |
| 13 | 351000 |
| Base | 213000 |
| '286 (1) | 309000 |
| '286 (2) | 436000 |
| Scrubbing Bubbles | 343000 |

Test Methods
Surface Spreading Method

The "transport rate factor" is measured as described below.

A 12"×12" pane of frosted or etched glass is mounted in a flat-bottomed basin that is large enough to support the pane of glass. The basin is provided with a means for drainage such that water does not accumulate on the surface of the pane of glass as the experiment is performed at a room temperature of approximately 22° C. in ambient conditions. The pane of glass is supported on top of the bottom of the basin of water using 4"×by 4" ceramic tiles—one tile at each side of the bottom edge of the pane. The middle 4 inches of the pane is not touching the bottom, so that water can run down and off the glass pane. The pane of glass is juxtaposed such that pane of glass is at an angle of approximately 39° from the bottom of the basin.

The glass pane is provided with 0.5 inch measurement markers from a first edge to the opposing edge.

A glass funnel (40 mm long×15 mm ID exit, to contain >100 ml) is provided approximately 3.5" over the 9" mark of the pane of glass.

The pane of glass is cleaned with room temperature water to remove trace surface active agents. The cleaned pane of glass is rinsed until there is no observable wave spreading on the pane.

A sample of approximately 7 g. (approximately 1.5" diameter circle for gels) of composition is applied to the pane of glass at the 0 mark. Four beakers (approximately 200 mL each) of water (are slowly poured over the top of the glass pane at the 9" height point and is allowed to run down the pane of glass to condition the composition.

After about one minute, the funnel is then plugged and is provided with approximately 100 mL of water. An additional 100 mL of water is slowly poured onto the glass pane at approximately the 9" marker. After approximately 10 seconds, the stopper is removed and a timer is started as the water in the funnel drains onto the pane of glass.

A wave on the surface of the draining water film above the composition is observed to creep up the glass and the time for the composition to reach the 5" marker is recorded.

The test is repeated for 10 replicates and the time in seconds is averaged and reported as the "transport rate factor" (time in seconds).

Adhesion Test

The ability of a composition to adhere to an exemplary hard surface is measured as described below.

A workspace is provided at a temperature of from about 86° F. to about 90° F. The relative humidity of the workspace is set to from about 40% to about 60%.

A board comprising twelve 4.25"×4.25" standard grade while glossy ceramic tiles arranged in a 3 (in the y-direction)×4 (in the x-direction) configuration (bonded and grouted) to a plexi-glass back is provided.

The board is rinsed with warm (about 75° F. to about 85 OF) tap water using a cellulose sponge. The board is then re-rinsed thoroughly with warm tap water. A non-linting cloth (ex. Kimwipe®, Kimberly Clark Worldwide, Inc., Neenah, Wis.) saturated with isopropanol is used to wipe down the entire tile board.

The board is juxtaposed to be in a horizontal position (i.e., such that the plane of the board is flat on the floor or lab bench).

Samples approximately 1.5" in diameter and weighing from about 5.5 g to about 8.0 g are provided to the surface of the board such that the bottom of the sample touches the top-most, horizontally oriented (i.e., in the x-direction), grout line of the board. Samples are spaced approximately 2" apart from each other. A permanent marker is used to draw a straight line (parallel to the x-direction) approximately 0.75" below the top-most grout line.

The board is juxtaposed to then be in the vertical position (i.e., such that the plane of the board is perpendicular with the floor or lab bench). A timer is started as the board is moved to the vertical position. The time that a sample takes for the sample to slide down the tile a distance of about 1.5 times the diameter of the sample is measured, recorded as the "sample adhesion time."

Viscosity Test

A Brookfield temperature controlled Cone/Plate Viscometer (Brookfield Engineering Laboratories, Inc., Middleboro, Mass.) is used according to the manufacturer's specifications. The specific parameters used on the device are: Shear rate of 10; C-25-1 Cone; and an 80° C. to 25° C. temperature ramp-down for 240 seconds. The device provides the viscosity measurement in Pascal seconds (Pa·s). This measurement is then converted to centipoise (cP) (1 Pa·s=1000 cP).

Gel Temperature Test

A Brookfield temperature controlled Cone/Plate Viscometer (Brookfield Engineering Laboratories, Inc., Middleboro, Mass.) is used according to the manufacturer's specifications. The specific parameters used on the device are: Shear rate of 10; C-25-1 Cone; and an 80° C. to 25° C. temperature ramp-down for 240 seconds. The gel temperature is reported as the temperature at which the composition transitions to a viscosity of greater than 100 cps as the composition cools.

EXAMPLE 1

Transport Along Water Film

To illustrate the surprising range and speed of the Marangoni effect provided by the composition of the invention, an experiment is described below.

A conventional white toilet bowl (Kohler Co., Kohler, Wis.) is cleaned twice using a conventional cleaner ("The Works" Toilet and Bathroom Cleaner (20% HCl)) and brush to insure that no material is present on the ceramic surface of the toilet bowl. A 5% solution of blue dye in water is sprayed onto the surface of the toilet bowl to provide an essentially even blue coating over the entire bowl surface above the water line. The dye remains a substantially uniform blue and is substantially stationary and non-moving upon visual observation for about one minute. The toilet is flushed and the dye rinsed away.

A sample of composition weighing approximately 7 g. as set out above as "Sample 2" is applied as a single dollop to one location in an upper side of the toilet bowl above the water line. The toilet is flushed so water runs down over the composition and along the inside surface of the toilet. Thereafter, the blue dye solution was again sprayed over the toilet bowl surface to cover the entire area above the water line as indicated by the blue color. Upon visual observation for about two minutes, it is observed that the blue dye moved away from the applied composition in all directions by material emanating from the composition as evident by the now visual white surface of the bowl. By the end of two minutes, the composition covered approximately one half of the bowl surface as evident from the essential absence of blue dye from the surface. Without wishing to be limited by theory, it is thought that the spread of the composition occurred through the Marangoni effect.

Due to the spread of the composition over the bowl, the desired action sought by the active agent(s) (e.g. cleaning, disinfecting and/or fragrancing) present in the composition is achieved over an extended area and provides residual benefit on the surface to prevent build up from subsequent use and prevent water stains.

EXAMPLE 2

Effect of Mineral Oil on Adhesion of Gel Compositions

Samples of compositions (approximately 7 g.) according to the present invention containing 0, 0.1, 0.5 and 1 wt. % (Samples E-H, respectively) are tested according to the Adhesion Test Method described herein. Two trials of each of Samples E-H is applied to a tile board according to the adhesion test method described below. FIGS. 2A-E are photographs of the tile board at times of 8.5 hours, 9.5 hours, 11 hours, 12.5 hours, and 15 hours, respectively. Surprisingly, it is discovered that the compositions with a relatively lower wt. % mineral oil tend to have lower adhesion times than samples with a relatively higher wt. % mineral oil.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention.

It is noted that terms like "specifically," preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

All documents cited in the Detailed Description of the invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

We claim:

1. A composition for treating a hard surface comprising
   (a) about 18 wt. % to about 80 wt. % of at least one adhesion promoter which causes a bond with water and is a linear or branched compound having at least one hydrophilic group capable of interaction with water molecules;
   (b) at least one surfactant selected from the group consisting of: anionic, nonionic, cationic, amphoteric, zwitterionic, and combinations thereof, wherein said at least one surfactant includes at least 7.5 wt. % of at least one nonionic surfactant, wherein said at least one nonionic surfactant can optionally also serve in part or all as (a);
   (c) mineral oil;
   (d) water;
   (e) optionally, at least one solvent;
   (f) optionally, a hydrophilic polymer;
   wherein each of the components of (a), (b), (c), (d), (e) and (f) of the composition are selected to be present in an amount so that upon combination said components provide the composition with properties of being a thickened gel having a viscosity of about 150,000 centipoise (cP) to about 400,000 cP, and self-adhesive to a vertical hard surface upon application to a vertical hard surface and said composition substantially adheres to the vertical hard surface through a plurality of periodic flows of rinse water such that said composition only partially dissolves upon each of the plurality of periodic flows of rinse water thereover thereby providing a wet film extending from and surrounding the composition when said composition is on said vertical hard surface and rinse water is passed over said composition and said vertical hard surface.

2. The composition of claim 1, wherein said at least one adhesion promoter is present in an amount of about 18 wt. % to about 27 wt. %; said at least one surfactant is present in an amount of about 7.5 wt. % to about 20 wt; said mineral oil is present in an amount of from greater than 0 to about 5 wt. %; said solvent is present in an amount of 0 to about 5 wt. %; said hydrophilic polymer is present in an amount of about 1 to about 10 wt. %, and a balance of water.

3. The composition of claim 1, wherein said hydrophilic polymer is present and serves to hold the composition to the vertical hard surface to extend spreading time and delivery of active agents to the hard surface.

4. The composition of claim 3, wherein said hydrophilic polymer is present in an amount of about 1 to about 10 wt. %.

5. The composition of claim 1 further comprising a superwetter compound which enhances spreading of the wet film.

6. The composition of claim 5, wherein said superwetter compound is present in an amount of 0 to about 5 wt. %.

7. The composition of claim 1, wherein said mineral oil is present in an amount of about 0.5 to 3.5 wt. %.

8. The composition of claim 2, wherein said mineral oil is present in an amount of about 0.5 to 3.5 wt. %.

9. The composition of claim 1, further comprising at least one active agent, wherein said active agent is one or more of a fragrance, germicide, antimicrobial, bleach, or deodorizer.

10. A composition for treating a hard surface, said composition comprising:
  (a) from about 18 wt. % to about 80 wt. % of one or more components, including at least one nonionic ethoxylated alcohol surfactant, which render the composition self-adhering to a vertical hard surface to be treated by said composition by causing a bond with water and providing the composition as a thickened gel or a solid wherein the thickened gel or the solid is substantially retained on said vertical hard surface under action of a plurality of periodic flows of rinse water;
  (b) from about 7.5 to about 20 wt. % of at least one anionic surfactant;
  (c) from greater than 0 to about 5 wt. % of mineral oil;
  (d) water; and
  (e) optionally at least one active agent,
  wherein said at least one anionic surfactant and said at least one nonionic ethoxylated alcohol surfactant are present in a combined amount to provide said composition with properties of (1) being self-adhesive to a vertical hard surface, and (2) being only partial dissolvable upon each of a plurality of flows of rinse water thereover, and (3) providing a wet film which emanates from said composition over a hard surface surrounding said composition, said wet film providing a delivery vehicle for components of said composition for immediate and residual treatment of said hard surface surrounding said composition, wherein (1), (2) and (3) are present under each of a plurality of periodic flows of water over said composition when adhered to a hard surface.

11. The composition of claim 10, further comprising a hydrophilic polymer which holds the composition to the hard surface to enhance maintenance and thereby extend spreading time and delivery of the at least one active agent.

12. The composition of claim 10, further comprising a superwetting compound which enhances spreading of the wet film.

* * * * *